United States Patent [19]

Keding et al.

[11] Patent Number: 5,034,535
[45] Date of Patent: Jul. 23, 1991

[54] PROCESS FOR S-METOPROLOL VIA OXAZOLIDIN-2-ONE

[75] Inventors: Britt I. Keding, Stockholm; Bo A. R. Lindqvist, Södertälje; Bengt B. Samuelsson, Onsala, all of Sweden

[73] Assignee: Astra Pharmaceutical Production Aktiebolag, Sodertalje, Sweden

[21] Appl. No.: 529,712

[22] Filed: May 30, 1990

Related U.S. Application Data

[63] Continuation of Ser. No. 341,787, Apr. 21, 1989, abandoned.

[30] Foreign Application Priority Data

Apr. 22, 1988 [SE] Sweden ................................ 8801518

[51] Int. Cl.$^5$ .......................................... C07D 233/02
[52] U.S. Cl. .................................. 548/232; 564/348; 560/205
[58] Field of Search ..................... 564/348; 548/232

[56] References Cited

U.S. PATENT DOCUMENTS

| | | | |
|---|---|---|---|
| 3,641,152 | 2/1972 | Shavel | 564/348 |
| 3,930,016 | 12/1975 | Berntsson et al. | 564/348 |
| 4,287,351 | 9/1981 | Bourgery et al. | 548/232 |
| 4,296,242 | 10/1981 | Nagabhushan | 548/232 |

FOREIGN PATENT DOCUMENTS

| | | | |
|---|---|---|---|
| 0064294 | 11/1981 | European Pat. Off. | |
| 2810732 | 9/1978 | Fed. Rep. of Germany | |
| 0067544 | 4/1982 | Japan | 564/348 |
| 0108870 | 5/1987 | Japan | 548/232 |

OTHER PUBLICATIONS

Chem. Abst. vol. 105, Entry 152694d (1986).
Chemical Abstracts, vol. 100, No. 21 21st May 1984 p. 598, No. 174473e. Columbus, Ohio, US; Maruko Pharmaceutical Co. Ltd.

Primary Examiner—Donald G. Daus
Attorney, Agent, or Firm—White & Case

[57] ABSTRACT

A process for preparing S-metoprolol of the formula

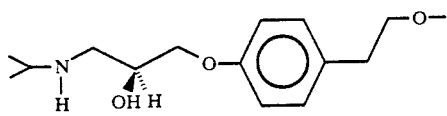

or a salt thereof, with high enantiomeric purity, is described, whereby a (S)-5-hydroxymethyl-3-isopropyloxazolidin-2-one sulfonic acid ester of the formula

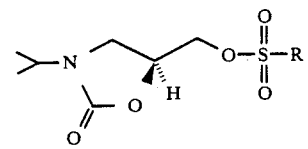

is prepared, and further reacted with 4-[2-methoxyethyl]phenol of the formula

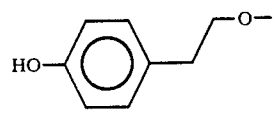

and the resulting intermediate of the formula

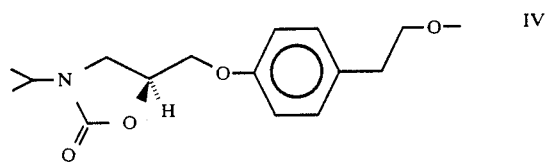

is hydrolysed to S-metoprolol, and whereby the (S)-5-hydroxymethyl-3-isopropyloxazolidin-2-one sulfonic acid ester of formula II is prepared by reacting (S)-3-isopropylamino-1,2-propanediol of the formula

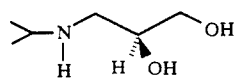

with a chloroformic acid ester of the formula

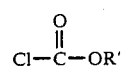

wherein R' is an alkyl group having 1–3 carbon atoms or a phenyl group, to the formation of (S)-5-hydroxymethyl-3-isopropyloxazolidin-2-one of the formula

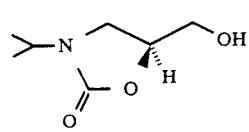

which is reacted with an activated sulfonic acid of the formula

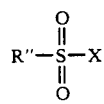

wherein R" is an aryl group such as tolyl and X is a halogen such as Cl, to formation of the ester of formula II, which when required is enriched with the (S)-enantiomer by crystallization.

8 Claims, No Drawings

PROCESS FOR S-METOPROLOL VIA OXAZOLIDIN-2-ONE

This application is a continuation of application Ser. No. 341,787, filed on Apr. 21, 1989 now abandoned.

TECHNICAL FIELD

The present invention is related to a novel process for preparing S-metoprolol, or a salt thereof, with high enantiomeric purity. The invention is also related to preparation of an intermediate employed in said process.

BACKGROUND ART

Metoprolol, having the formula

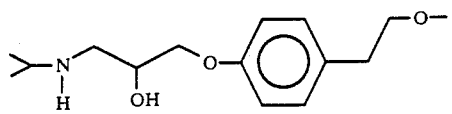

is a wellknown pharmaceutical compound having a strongly selective blocking effect on the cardiac $\beta_1$-receptors in animals and man, and being used inter alia in the treatment of hypertension, cardiac arrhythmias, angina pectoris and migraine. It is a well established fact that in metoprolol, like in other $\beta$-blockers the $\beta$-blocking effect resides only in the S-enantiomer, while possibly occurring side effects may reside in either or both enantiomers.

S-metoprolol and a process for preparation thereof is described inter alia in EP-A2-0 179 031.

DESCRIPTION OF THE INVENTION

The object of the present invention is to obtain a process for preparing S-metoprolol with very high enantiomeric purity. A further object is to obtain such a process enabling an economical and convenient preparation of S-metoprolol.

The invention is related to a process for preparing S-metoprolol of the formula

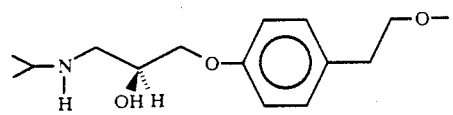

or a salt thereof, with high enantiomeric purity, whereby a (S)-5-hydroxymethyl-3-isopropyloxazolidin-2-one sulfonic acid ester of the formula

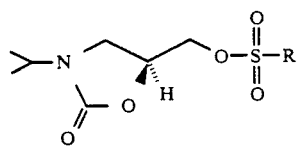

is prepared, and further reacted with 4-[2-methoxyethyl]phenol of the formula

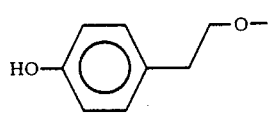

and the resulting intermediate of the formula

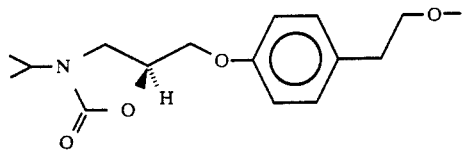

is hydrolysed to S-metoprolol. The novel process is characterized in that the (S)-5-hydroxymethyl-b 3-isopropyloxazolidin-2-one sulfonic acid ester of formula II is prepared by reacting (S)-3-isopropylamino-1,2-propanediol of the formula

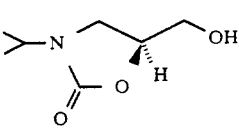

with a cholorformic acid ester of the formula

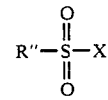

wherein R' is an alkyl group having 1-3 carbon atoms or phenyl group, to the formation of (S)-5-hydroxymethyl-3-isopropyloxazolidin-2-one of the formula

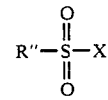

which is reacted in a manner known per se with an activated sulfonic acid of the formula $$R''-\overset{O}{\underset{O}{\overset{\|}{S}}}-X$$

wherein R" is an aryl group such as tolyl and X is a halogen such as Cl, to formation of the ester of formula II, which when required is enriched with the (S)-enantiomer by crystallization.

By the present invention a S/R enantiomeric ratio of metoprolol greater than 99.0/1.0 may be obtained. The ratio 99.0/1.0 is expected to become a standard ratio for S-metoprolol as a pharmaceutical. The desired ratio is achieved by preparing the intermediate of formula II with high enantiomeric purity. It is an important finding by the inventors that said intermediate will be enriched with the S-enantiomer or crystallization. Thus, according to preferred embodiments of the invention, S-metoprolol with at least the desired enantiomeric ratio is obtained either by using the starting compound of formula V with a S/R enantiomer ratio of at least 95/5, and making several recrystallizations of the subsequently obtained intermediate II, or by using said starting compound with a S/R enantiomer ratio of at least 98/2, whereby normally a single crystallization of the intermediate II will suffice.

Furthermore, the inventors have found that the step of synthesis of the compound of formula VII proceeds without substantial racemization.

The starting material of formula V may be obtained by several routes such as reacting (R)-3-chloro-1,2-propanediol of the formula

 VIII which compound is described in Agric. Biol. Chem. 46 (1982) 1153, with isopropylamine in the presence of potassium carbonate in isopropyl alcohol. (It will of course be realized that compound VIII in R-form and compound V in S-form have the same configuration around the asymmetric carbon atoms, although the terminology is different.) This synthesis proceeds without substantially changing the enantiomeric ratio. Thus, the process of the invention may suitably be started with the compound of formula VIII with the same enantiomeric ratio as required for the compound of formula V. There will then usually not be any need to isolate the compound of formula V.

The process of the invention may suitably be carried out under the following conditions

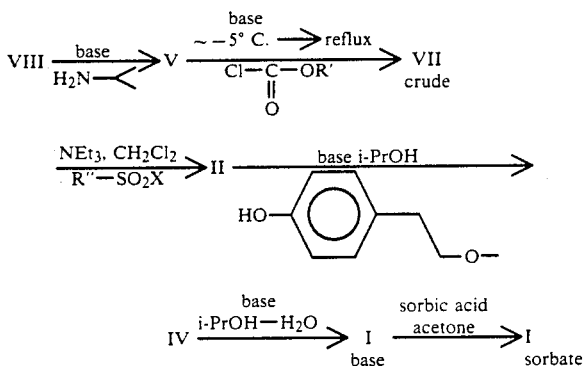

A further aspect of the invention is a process for preparing the intermediate of formula II, said process comprising the reaction steps V to VII to II as described above.

Pharmaceutical preparations of S-metoprolol and salts thereof, and of the sorbate in particular may be obtained as known for racemic metoprolol, and in particular as known from EP-A1-0 220 143. It will of course be realized that only half the amount of active compound will be required for a dosage unit, as compared with racemic metoprolol.

Pharmaceutically acceptable acid addition salts of S-metoprolol will be evident for one of ordinary skill in the art and include, but are not limited to those known for racemic metoprolol, and in particular the sorbate, succinate and tartrate.

The invention is further illustrated by the following examples:

EXAMPLE 1

Step 1. (S)-3-isopropylamino-1,2-propandiol (compound 1)

A mixture of potassium carbonate (5.60 kg, 40.5 mol), water (1.10 kg, 61.1 mol) and isopropanol (23 l) was stirred at room temperature for two and a half hours. The formation of potassium carbonate sesquihydrate was checked using TGA.

(R)-3-chloro-1,2-propandiol (4.50 kg, 40.7 mol) was subsequently added and the mixture cooled to 10° C. Isopropyl amine (16.8 kg, 284 mol) was added during 30 minutes. After completed addition the mixture was heated to 40° C. and stirred for 14 hours, after which the temperature was increased to 45° C. and stirred for another six hours to complete the reaction.

The mixture was filtered, the solids were washed with isopropanol (25 l) and the filtrate was evaporated in vacuo.

Isopropanol (30 l) was added to the resulting oil, and the solution was evaporated in vacuo to yield (S)-3-isopropylamino-1,2-propandiol as an oil. The product was used directly in the following step without further purification.

Purity GC: 94%.

Water content: 1.3% (w/w) (Karl Fischer).

Step 2.
(S)-5-hydroxymethyl-3-isopropyl-oxazolidin-2-one (compound 2)

Potassium carbonate (6.10 kg, 44.1 mol), water (1.03 kg, 57.2 mol) and isopropanol (15 l) were added to the oily (S)-3-isopropylamino-1,2-propandiol. The mixture was stirred at room temperature for three hours. The formation of potassium carbonate sesquihydrate was checked using TGA.

Ethyl chloroformate (3.94 kg, 36.3 mol) was added during one hour to the cooled mixture, keeping the temperature at −5° C. After completed addition, the mixture was stirred for another two hours at −5° C. The mixture was then heated to reflux (83° C.), stirred for 18 hours and filtered. The solids were washed with isopropanol (15 l) and the filtrate was evaporated in vacuo to yield a yellow oil. Toluene (20 l) was added and the resulting solution was evaporated in vacuo. This was repeated once, yielding (S)-5-hydroxymethyl-3-isopropyl-oxazolidin-2-one as a semicrystalline oil containing <1% of isopropanol. The product was used directly in the following step without further purification.

Purity GC: 94%.

Step 3.
(S)-3-isopropyl-5-p-toluenesulfonyloxymethyl-oxazolidin-2-one (compound 3)

To a stirred solution of (2) and triethylamine (4.70 kg, 46.4 mol) in methylene chloride (25 l) at 0° C., p-toluenesulfonylchloride (7.65 kg, 40.1 mol) was added during 30 minutes. The mixture was stirred for 20 hours at room temperature and then quenched by adding water (8 l). The aqueous layer was separated off and the organic phase was washed with aqueous sodium bicarbonate (4 l, 5%), followed by water (4 l) adjusted to pH=4 with hydrochloric acid (6M, 0.9 l). The organic phase was dried with sodium sulfate (0.65 kg), filtered and evaporated to give an oil. Isopropanol (10 l) was added to give a slurry, which was evaporated in vacuo once more.

Isopropanol (36 l) was added and the slurry was heated to 40° C. The resulting solution was allowed to cool slowly to −5° C. The crystals were filtered off and washed with cold isopropanol (10 l), yielding 13.84 (wet weight) of (S)-3-isopropyl-5-p-toluenesulfonyloxymethyl-oxazolidin-2-one. This corresponds to 7.90 kg of dry weight (62% from (1)).

Melting point: 75° C.

Purity GC: 93–96%.

Purity TLC: one minor impurity.

Optical rotation: $[\alpha]_D^{20.3} = +53.7°$ (C=0.90 CHCl$_3$).

Step 4. (S)-metoprolol base or (S)-1-isopropylamino-3-[p-(2-methoxyethyl)phenoxy]-2-propanol (compound 4)

Potassium carbonate (4.70 kg, 34.0 mol), water (0.90 kg, 50.0 mol) and isopropanol (66 l) were stirred at room temperature for two hours. 2-Methoxyethylphenol (5.17 kg, 34.0 mol) in isopropanol (3.5 l), followed by (3) (13.84 kg (wet), 25.2 mol) were added. The mixture was heated to reflux (83° C.) and stirred for 18 hours. GC and TLC indicated a complete conversion giving (S)-3-isopropyl-5-[4-(2-methoxyethyl)-phenoxymethyl]-oxazolidin-2-one. To the refluxing mixture, potassium hydroxide (7.30 kg, 130 mol) in water (9.1 kg) was added. The mixture was stirred, still at reflux, for another 20 hours, filtered and the filtrate was evaporated in vacuo. Toluene (15 l) was added and the solution was evaporated in vacuo, to yield an oil. Toluene (30 l) and water (8 l) were added to the oil and the two-phase system was stirred for one hour. The aqueous phase was separated off. To the organic phase, water (30 l) and sulfuric acid (6M, 1.75 l) were added to give pH 5. The organic phase was separated off and toluene (30 l) was added to the aqueous phase. Sodium hydroxide (45%, 1.40 l) was added to give pH>12 and the aqueous phase was separated off. The organic phase was washed with water (5 l) and evaporated in vacuo to yield an oil. Acetone (20 l) was added and the solution was evaporated in vacuo. This was repeated twice and finally the oil was diluted with 20 liters of acetone, yielding 36.35 kg of a solution containing 0.53 mol of metoprolol base per kg of solution (76% from (3)).

Purity GC: 90%.

Step 5. (S)-metoprolol sorbate or (S)-1-isopropylamino-3-[p-(2-methoxyethyl)-phenoxy]-2-propanol sorbate (compound 5)

To the stirred acetone solution of metoprolol base (19.3 mol), acetone (30 l) and sorbic acid (2.12 kg, 18.9 mol) were added at room temperature. The mixture was heated to reflux and the hot solution was filtered. The filtrate was allowed to cool slowly to 0° C. The crystals were centrifugated off, washed with cold acetone (10 l) and dried for three days in vacuo at room temperature to yield 5.95 kg of crystalline (S)-metoprolol. (81% from (4)).

Melting point: 113° C.
Purity GC: 100.0%.
Purity HPLC: 100.0%.
R/S (HPLC): 0.1/99.9.

By concentrating the mother liquor, an additional 560 g of (S)-metoprolol sorbate was obtained. (7% from (4)).

Purity HPLC: 99.9%.
R/S (HPLC): 0.0/100.0.

Giving a total yield of 88% from (4).

EXAMPLE 2

Example 1 was repeated in laboratory scale with different R/S enantiomeric ratios of compound 1.

| Compound 1 | R/S: | 10/90 | 5.0/95.0 | 2.4/97.6 |
|---|---|---|---|---|
| | | ↓ | ↓ | ↓ |
| Compound 2 | Yield: | 75% | 74% | 71.% |
| | | ↓ | ↓ | ↓ |
| Compound 3 | Yield: | 55% | 64% | 62% |
| | [α]$_D^{20}$: | +42.4° | +47.6° | +52.7° |
| | | | ↘ | |
| Compound 3 recrystallized | Yield: [α]$_D^{20}$: | | 83% +48.9° | |
| | | ↓ | ↓ | ↓ |
| Compound 5 (S-metoprolol sorbate) | R/S: | 9.5/90.5 | 3.5/96.5 3.0/97.0 | 0.1/99.9 |

We claim:
1. A process for preparing s-metoprolol having the formula:

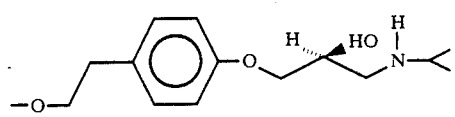

or a salt thereof with high enantiomeric purity, comprising the steps of:
a) reacting (s)-3-isopropylamino-1,2-propanediol having the formula:

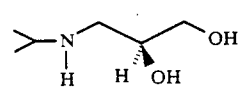

with a chloroformic acid ester having the formula:

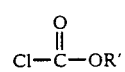

wherein R' is an alkyl group having 1–3 carbon atoms or a phenyl group to form (s)-5-hydroxymethyl-3-isopropyloxazolidin-2-one having the formula:

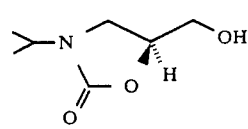

b) reacting the resulting compound from step a), having the formula VII with an activated sulfonic acid having the formula:

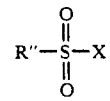

wherein R' is tolyl and X is Cl, to form the sulfonic acid ester of the compound having formula II;
c) enriching the amount of the compound having formula II from step b by crystallization of the ester;

d) reacting the crystallized compound having formula II with 4-[2-methoxyethyl] phenol having the formula:

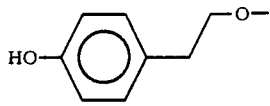

e) hydrolysing the resulting compound having the formula:

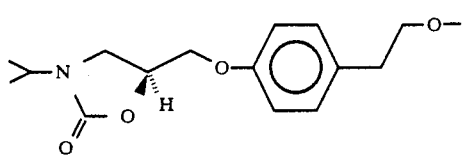

to form s-metoprolol.

2. The process according to claim 1 wherein repeated recrystallization are carried out in step c).

3. The process according to claim 1 wherein the (s)-3-isopropylamino-1,2-propanediol has an S/R enantiomeric ratio of at least 98/2 and the (s)-metoprolol or salt formed has an S/R enantiomeric ratio greater than 99.0/1.0.

4. The process according to claim 2 wherein the s metoprolol or salt formed has an S/R enantiomeric ratio greater than 99.0/1.0.

5. The process according to claim 1 wherein the (s)-3-isopropylamino-1,2-propanediol has an S/R enantiomeric ratio of at least 95/5 and the (s)-metoprolol or salt formed has an S/R enantiomeric ratio greater than 99.0/1.0.

6. A process according to claims 1-5 wherein the compound having the formula V is isolated as the Sorbate.

7. A process for preparing a (S)-5-hydroxymethyl-3-isopropyloxazolidin-2-one sulfonic acid ester having the formula:

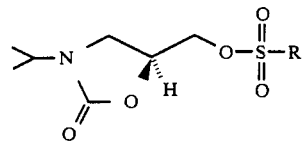

or a salt thereof, with high enantiomeric purity, comprising a) reacting (S)-3-isopropylamino-1,2-propanediol having the formula:

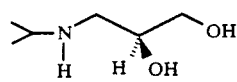

with a chloroformic acid ester having the formula:

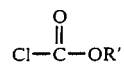

wherein R' is an alkyl group having 1-3 carbon atoms or a phenyl group, to the form of (S)-5-hydroxymethyl-3-isopropyloxazolidin-2-one having the formula:

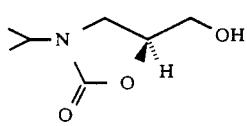

and b) reacted the compound having formula VII with an activated sulfonic acid having the formula:

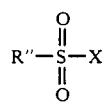

wherein R is tolyl and X is Cl, to form the ester of the compound having formula II and c) enriching the amount of the compound having formula II from step b) by crystallization of the ester.

8. The process according to claim 7 wherein repeated recrystallizations are carried out in step c).

* * * * *